(12) United States Patent
Suehara

(10) Patent No.: US 10,596,363 B2
(45) Date of Patent: Mar. 24, 2020

(54) MEDICAL TREATMENT TOOL

(71) Applicant: TERUMO KABUSHIKI KAISHA, Tokyo (JP)

(72) Inventor: Satoru Suehara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 267 days.

(21) Appl. No.: 15/582,344

(22) Filed: Apr. 28, 2017

(65) Prior Publication Data

US 2017/0232233 A1   Aug. 17, 2017

Related U.S. Application Data

(63) Continuation of application No. 14/219,594, filed on Mar. 19, 2014, now Pat. No. 9,669,204, which is a continuation of application No. PCT/JP2012/068179, filed on Jul. 18, 2012.

(51) Int. Cl.

| | |
|---|---|
| *A61M 29/00* | (2006.01) |
| *A61M 39/08* | (2006.01) |
| *A61M 25/01* | (2006.01) |
| *A61M 29/02* | (2006.01) |
| *A61B 1/005* | (2006.01) |
| *A61B 1/04* | (2006.01) |
| *A61M 25/10* | (2013.01) |

(52) U.S. Cl.
CPC ............. *A61M 39/08* (2013.01); *A61B 1/005* (2013.01); *A61B 1/04* (2013.01); *A61M 25/0138* (2013.01); *A61M 25/0147* (2013.01); *A61M 29/00* (2013.01); *A61M 29/02* (2013.01); *A61M 2025/1093* (2013.01); *A61M 2210/0618* (2013.01); *A61M 2210/0681* (2013.01)

(58) Field of Classification Search
CPC .. A61M 25/10; A61M 25/0138; A61M 29/00; A61M 29/02
See application file for complete search history.

(56) References Cited

U.S. PATENT DOCUMENTS

| | | |
|---|---|---|
| 2004/0102719 A1 | 5/2004 | Keith et al. |
| 2009/0131865 A1 | 5/2009 | Partlett et al. |

FOREIGN PATENT DOCUMENTS

| | | |
|---|---|---|
| JP | 5-41502 U | 6/1993 |
| JP | 2002-095627 A | 4/2002 |
| JP | 2008-508063 A | 3/2008 |

OTHER PUBLICATIONS

International Search Report dated Sep. 25, 2012 in related application PCT/JP2012/068179 with English-language translation (2 pgs.).

*Primary Examiner* — Melanie R Tyson
(74) *Attorney, Agent, or Firm* — Foley & Lardner LLP

(57) ABSTRACT

A medical treatment tool includes a bendable tube configured to be inserted into a body of a patient; an operating body disposed in the bendable tube and configured to cause bending of the bendable tube, the operating body including: a plurality of divided members that are divided from each other along axially extending edges of adjacent divided members, portions of the divided members forming a tubular structure, and an annular connecting portion, an outer surface of the annular connecting portion being continuous with outer surfaces of the divided members; and a cylindrical member located inside the operating body. Each divided member includes at least one cutout portion formed between the tubular structure and the annular connecting portion. The cylindrical member is in contact with inner surfaces of the divided members.

9 Claims, 14 Drawing Sheets

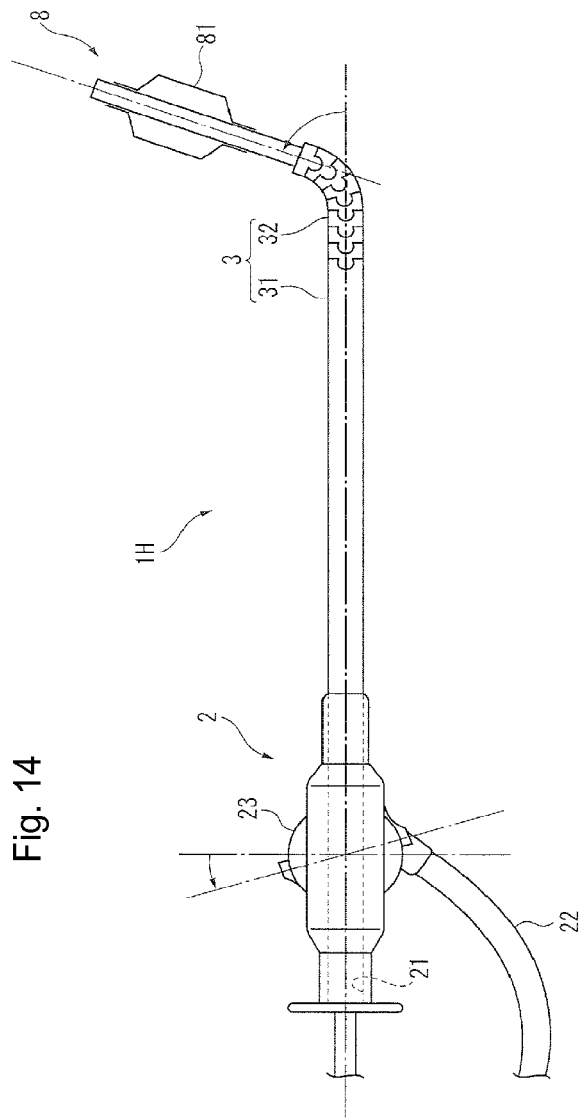

MEDICAL TREATMENT TOOL

CROSS-REFERENCE TO RELATED APPLICATIONS

This application is a continuation filed under 35 U.S.C. § 111(a) claiming the benefit under 35 U.S.C. § 120 of U.S. patent application Ser. No. 14/219,594, filed Mar. 19, 2014, which is a continuation filed under 35 U.S.C. § 111(a) claiming the benefit under 35 U.S.C. §§ 120 and 365(c) of PCT International Application No. PCT/JP2012/068179 filed on Jul. 18, 2012, the entire contents of which are hereby incorporated by reference in their entireties.

BACKGROUND

Technical Field

The present disclosure relates to a medical treatment tool.

Background Art

In the related art, a medical treatment tool in which an insertion section to be inserted inside the body is configured to be bendable and the insertion section is configured to bend during operation by an operating member, such as a wire, is known (for example, refer to JP-UM-A-5-41502).

The medical treatment tool described in JP-UM-A-5-41502 includes a pair of mutually facing narrow plate spring members, a fiber that is arranged along an axial direction between plate surfaces of the pair of plate spring members and that has a distal portion anchored to a distal portion of each plate spring member, and a jacket member that covers the pair of plate spring members and the fiber. The fiber is configured to bend during operation by moving the pair of plate spring members mutually in opposite directions.

In a medical treatment tool including an insertion tube having an inner cavity, such as a catheter, the insertion tube is made to bend during operation by fixing a wire or the like to the distal portion of the insertion tube.

However, when the wire or the like is fixed to the distal portion of the insertion tube, the wire or the like can block the inner cavity when the insertion tube is bent, in which case the inner cavity will not be secured. For this reason, a guide portion, such as a guide hole that guides the wire or the like, must be provided. The wire or the like needs to be held at a predetermined position, which complicates the structure of the device.

Therefore, there is a need for a medical treatment tool in which an inner cavity of an insertion tube can be secured with a simple structure.

SUMMARY OF THE INVENTION

In one embodiment, a medical treatment tool includes an insertion tube that is provided to be bendable and is inserted inside the body of a patient; and an operating body that is provided in the insertion tube and makes the bending of the insertion tube occur. The operating body includes a plurality of divided members that are divided in a circumferential direction to form a tubular structure in the insertion tube; and a connecting portion that connects distal portions of the respective divided members in an axial direction of the tubular structure. The divided member includes a cutout portion formed as an end edge in the circumferential direction.

According to this embodiment, the operating body forms the tubular structure by the plurality of divided members that are divided in the circumferential direction, and each divided member is provided with the cutout portion formed such that the end edge thereof in the circumferential direction is cut out. For this reason, the operating body can be bent in a low-rigidity portion where the cutout portion is provided, and the tubular structure of the operating body can be maintained in a high-rigidity portion where the cutout portion is not provided. Accordingly, since the operating body can be prevented from obstructing the inner cavity while enabling the bending of the insertion tube by the operating body, the inner cavity of the insertion tube can be secured with simple structure.

In one aspect, an inner surface of the insertion tube and an outer surface of the operating body slide on each other at least partially in the axial direction.

According to this aspect, since the inner surface of the insertion tube and the outer surface of the operating body slide on each other at least partially in the axial direction, the tubular structure of the operating body can be enlarged to the extent that the operating body can come into contact with the inner surface of the insertion tube. Accordingly, since a large space can be secured inside the operating body, the inner cavity of the insertion tube can be sufficiently secured.

Additionally, as the inner surface of the insertion tube and the outer surface of the operating body slide on each other, the operating body is regulated in the direction of an axial center by the insertion tube. Therefore, the operating body can be reliably arranged, and the inner cavity of the insertion tube can be sufficiently secured.

In one aspect, the plurality of divided members slide on each other at the end edges of the adjacent divided members in the circumferential direction.

According to this aspect, since the end edges of the adjacent divided members slide on each other in the circumferential direction, the tubular structure of the operating body can be reliably maintained by the abutment between the end edges of the divided members in the circumferential direction, while the relative movement in the axial direction between the divided members produced during the bending of the insertion tube is allowed by the sliding. Accordingly, the operating body can be prevented from blocking the inner cavity of the insertion tube during the bending of the insertion tube.

In one aspect, a plurality of the cutout portions are provided in the axial direction of each divided member.

According to this aspect, since the plurality of cutout portions are provided in the axial direction of each divided member, the operating body can be intermittently bent at the positions on the respective cutout portions. For this reason, since the bent shape of the insertion tube can be changed by changing the arrangement of the cutout portions in the axial direction, the bent shape of the insertion tube can be set according to a path into which the insertion tube is inserted.

In one aspect, the cutout portion is formed so that the circumferential dimension of the portion of each divided member where the cutout portion is provided becomes gradually smaller toward the axial direction.

According to this aspect, since the portion of each divided member where the cutout portion is provided becomes gradually narrow toward the axial direction, the rigidity of the portion can be changed according to the degree of narrowness of the portion. For this reason, since the bent shape of the insertion tube can be changed by changing the degree of narrowness of the portion, the bent shape of the insertion tube can be set according to a path into which the insertion tube is inserted.

In one aspect preferably, each divided member includes a movement regulating portion that regulates the relative movement of the adjacent divided members in the axial direction to a predetermined movement amount.

According to this aspect, since the movement regulating portion that regulates the relative movement of the adjacent divided members in the axial direction to a predetermined amount is provided, the bending amount of the insertion tube can be regulated to a predetermined amount, and the bending limit of the insertion tube can be defined.

In one aspect, the medical treatment tool further includes an annular member provided inside the operating body.

According to this aspect, since the annular member is provided inside the operating body, the tubular structure of the operating body can be maintained by the annular member even when there is a gap between the end edges of the adjacent divided members in the circumferential direction. On the other hand, when there is no gap between the end edges of the adjacent divided members in the circumferential direction, the tubular structure of the operating body can be more reliably maintained by the annular member. Accordingly, the inner cavity of the insertion tube can be secured irrespective of the presence or absence of the gap between the end edges of the divided members.

In one aspect, the medical treatment tool further includes a dilation body that is provided at an outer periphery of the insertion tube and dilates in a radial direction of the insertion tube.

According to this aspect, since the dilation body can be dilated in the narrow segment in the body, the narrow segment can be dilated and treated.

In one aspect, the medical treatment tool further includes a dilation body that is removably inserted into the tubular structure of the operating body and dilates in a radial direction of the insertion tube.

According to this aspect, since the dilation body is removably inserted into the tubular structure of the operating body, it is not necessary to provide the dilation body at the outer periphery of the insertion tube. For this reason, the insertion tube can be easily inserted inside the body in the dilation treatment of narrow segment.

In one aspect, the medical treatment tool is a treatment tool for treating rhinosinusitis.

According to this aspect, since the inner cavity of the insertion tube can be secured with simple structure in the medical treatment tool used for the treatment of the paranasal sinus, the manufacturing costs of the treatment tool used for the paranasal sinus can be reduced, an insert, such as an endoscope required for the treatment of the paranasal sinus, can be inserted into the insertion tube, or a fluid, such as a physiological salt solution, can be carried via the insertion tube.

BRIEF DESCRIPTION OF DRAWINGS

FIG. 14 is a plan view of a medical treatment tool related to a ninth embodiment of the invention.

DETAILED DESCRIPTION

Figure 1:
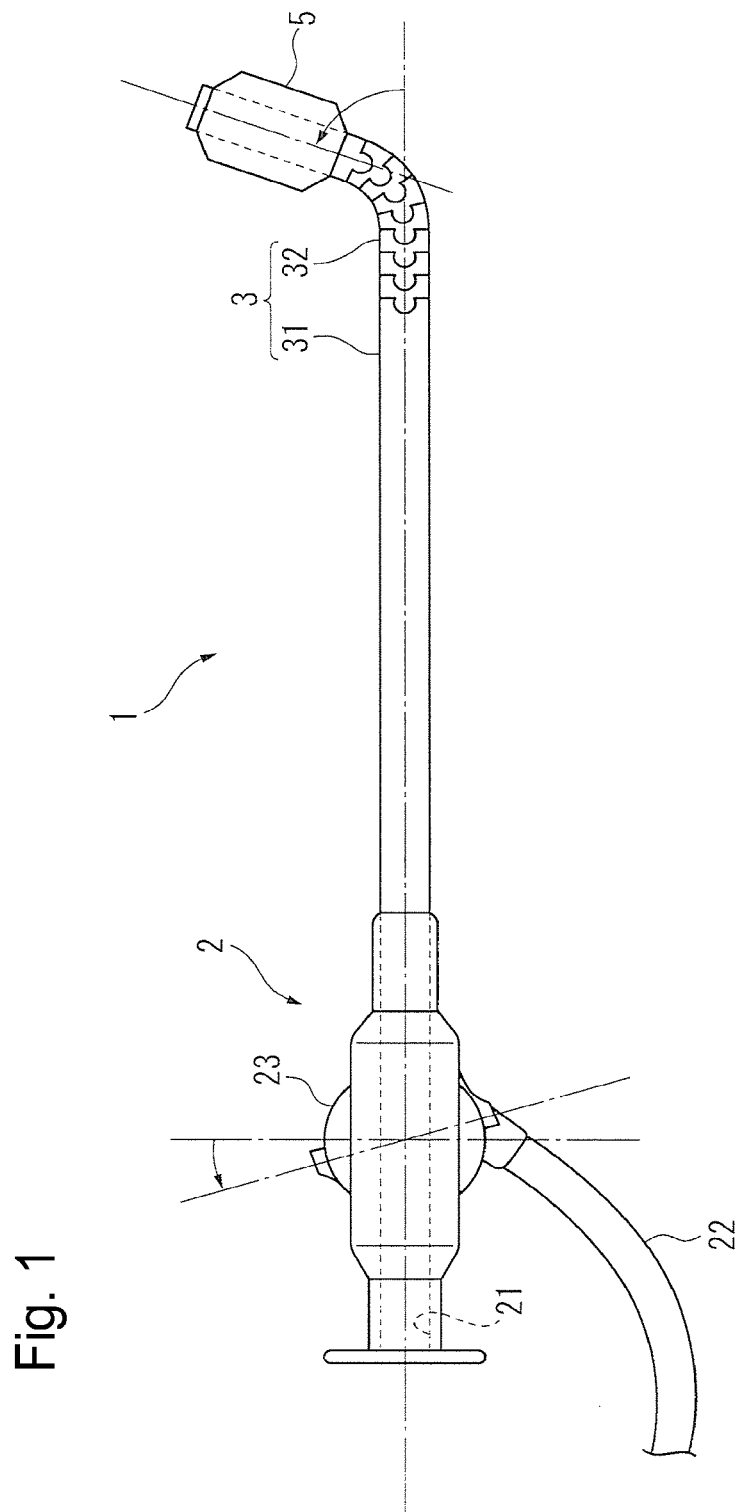
FIG. 1 is a plan view of a medical treatment tool related to a first embodiment of the invention.

Hereinafter, respective embodiments of the invention will be described with reference to the drawings.

In the embodiments following the second embodiment, the same component members as component members described in the first embodiment and component members having the same functions as the component members of the first embodiment will be designated using the same reference numerals as the component members of the first embodiment, and the descriptions thereof will be omitted or simplified.

First Embodiment

In FIG. 1, a medical treatment tool 1 related to the present embodiment includes a hub 2, an insertion tube 3 of which at least a portion is provided to be bendable and that is inserted inside the body of a patient, an operating body 4 (FIGS. 2 and 3) that is provided in the insertion tube 3 to operate bending of the insertion tube 3, and an dilation body 5 that is provided at an outer periphery of the insertion tube 3 and is dilated in the radial direction of the insertion tube 3.

The hub 2 includes an introduction path 21 that allows the inner cavity of the insertion tube 3 and the outside to communicate with each other and is configured so as to be capable of introducing a treatment tool, such as an endoscope, into the inner cavity of the insertion tube 3, a fluid carrying path 22 that is provided to branch from the introduction path 21 and is configured so as to be capable of carrying a fluid, such as a physiological salt solution, into the body and capable of carrying a fluid in the body to the outside, and a position fixture 23 that is rotatably provided at the hub 2 and fixes the bending position of the insertion tube 3 by the operating body 4.

Figure 2:
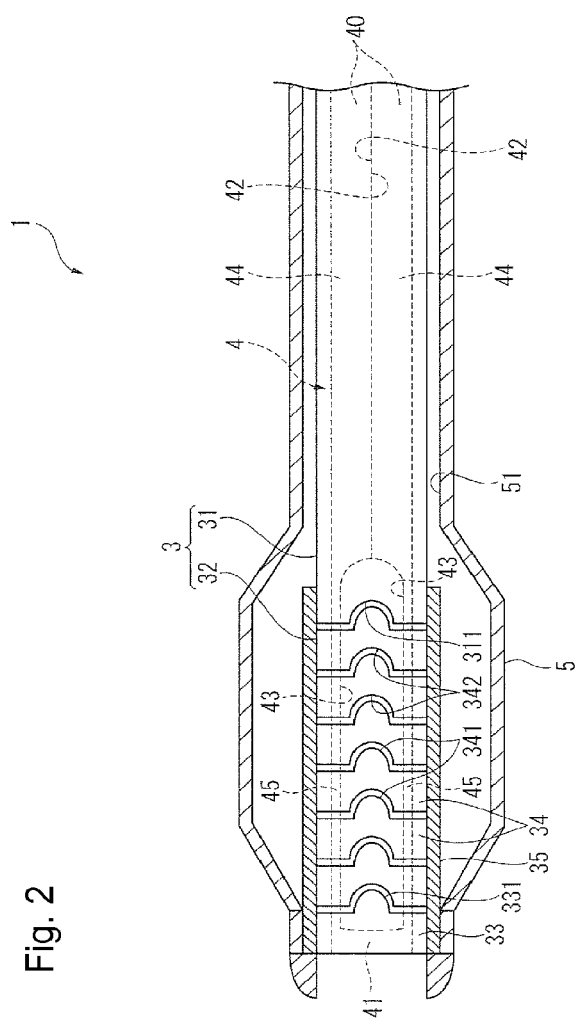
FIG. 2 is a partial cross-sectional side view showing an insertion tube of the medical treatment tool of FIG. 1.
Figure 3:
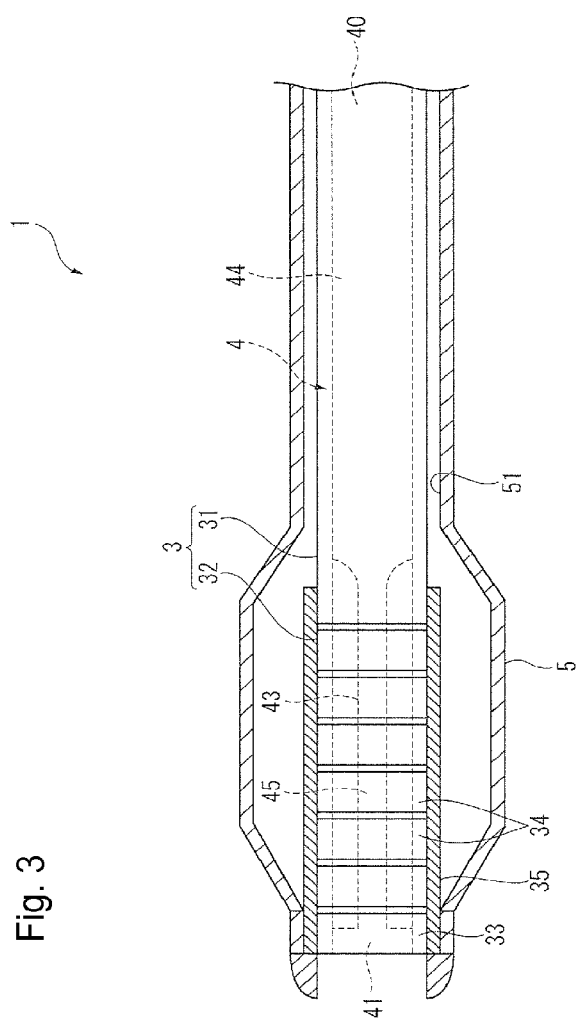
FIG. 3 is a partial cross-sectional side view showing the insertion tube of the medical treatment tool of FIG. 1.

The insertion tube 3, as shown in FIGS. 2 and 3, includes a rigid tube 31 that has a proximal portion connected to the hub 2, and a flexible tube 32 connected to a distal portion of the rigid tube 31. The flexible tube 32 includes a plurality of tubular bodies 33 and 34, and the tubular bodies 33 and 34 and the rigid tube 31 are coupled together in an axial direction so as to be mutually rotatable. Since an outer periphery of the flexible tube 32 is brought into close contact with and covered with a tubular member 35 having flexibility, such as an elastic member, a fluid sent to the dilation body 5 does not flow into the flexible tube 32 from a gap between each tubular body 33 or 34 and the rigid tube 31.

The respective tubular bodies 33 and 34 include rotating shaft portions 331 and 341 protruding in coupling directions (axial directions of the respective tubular bodies 33 and 34) from one-side end edges in the coupling directions.

On the other hand, the rigid tube 31 and the tubular member 34 include rotating supporting portions 311 and 342 formed such that the other-side end edges thereof in the coupling directions (the axial directions of the rigid tube 31 and the tubular member 34) retreat, and the rotating shaft portions 331 and 341 of the respective tubular bodies 33 and 34 are supported by the rotating supporting portions 311 and 342.

In addition, a pair of the rotating shaft portion 331 or 341 and the rotating supporting portion 311 or 342 are provided at positions that are symmetrical to each other with respect to the central axes of the rigid tube 31 and each tubular body 33 or 34.

The insertion tube 3 as described above is obtained, for example, by performing laser processing on a circular tubular member made of stainless steel. When the laser processing is used, the insertion tube 3 in a state where the rigid tube 31 and the respective tubular bodies 33 and 34 are coupled to each other can be easily obtained by simply cutting the circular tubular member with a laser. In addition, the material and manufacturing method of the insertion tube 3 are not limited to the above, and arbitrary materials and manufacturing methods can be used.

Figure 4:
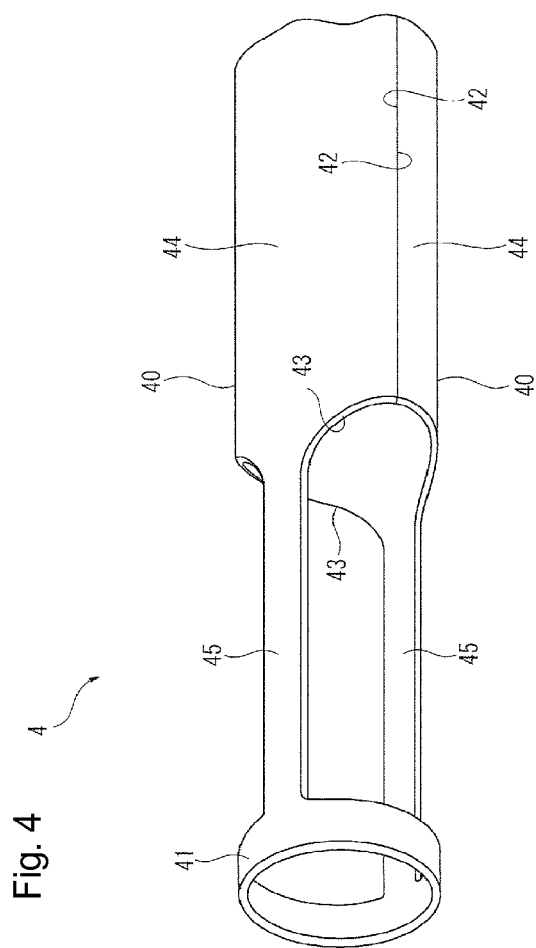
FIG. 4 is a perspective view of an operating body of the medical treatment tool of FIG. 1.

The operating body 4, as shown also in FIG. 4, includes a plurality of divided members 40 that are divided in a circumferential direction in the insertion tube 3 to form a tubular structure, and a connecting portion 41 that is formed in an annular shape and connects the distal portions of the respective divided members 40 in an axial direction of the tubular structure.

All of the plurality of divided members 40 are formed in the same shape. Each divided member 40 includes cutout portions 43 formed such that end edges 42 of the divided member 40 in the circumferential direction are cut out, a broad portion 44 that is a portion in which the cutout portions 43 of the divided member 40 are not provided and that has a shape such that a cylindrical member is divided in the circumferential direction, and a narrow portion 45 in which the cutout portions 43 of the divided member 40 are provided and that is formed so as to be narrower than the broad portion 44 by the cutout portions 43.

The cutout portions 43 are formed such that the end edges 42 on both sides in the circumferential direction are cut out in the same shape at the same position in the axial direction. In addition, in the present embodiment, the cutout portions 43 are formed at a portion between the connecting portion 41 and the broad portion 44.

The broad portion 44 is formed in a shape such that the cylindrical member is equally divided into two in the circumferential direction. The end edges 42 of the broad portion 44 in the circumferential direction are formed linearly, and slide on the end edges 42 of the adjacent of the divided member 40 in the axial direction. That is, the respective divided members 40 are formed so that the end edges 42 in the circumferential direction except the cutout portions 43 slide on each other in the axial direction.

The narrow portion 45 is provided at a substantially middle position of each divided member 40 in the circumferential direction so as to extend in the axial direction, and is formed such that the dimension thereof in the circumferential direction is constant. The narrow portions 45 of the respective divided members 40 are provided at positions that face each other across the center of the tubular structure.

In the above operating body 4, one divided member 40 and the other divided member 40 relatively move in the axial direction, whereby the two narrow portions 45 that face each other are bent within a plane passing through the two narrow portions 45 to bend the flexible tube 32. For this reason, the operating body 4 is arranged in the insertion tube 3 so that the narrow portions 45 are located between the mutually facing rotating shaft portions 331 and 341 of the flexible tube 32, that is, so that the cutout portions 43 are located at the positions of the rotating shaft portions 331 and 341.

Here, it is desirable that the external diameter of the operating body 4 be increased in order to increase the diameter of the inner cavity of the insertion tube 3. For this reason, the operating body 4 is adapted to have a size such that an outer surface thereof comes into contact with an inner surface of the insertion tube 3.

Moreover, it is desirable to make the thickness of the operating body 4 as small as possible due to the same reason. For this reason, the thickness of the operating body 4 is set to about 0.05 to 1.0 [mm], and desirably about 0.075 to 0.3 [mm].

Such an operating body 4 is easily obtained, for example, by performing laser processing on the circular tubular member made of stainless steel, similar to the case of the insertion tube 3. In addition, the material and manufacturing method of the operating body 4 are not limited to the above, and arbitrary materials and manufacturing methods can also be used.

The dilation body 5 is made of a flexible material, such as a polymer. The inside of the dilation body 5 communicates with a flow channel 51 provided around the insertion tube 3, and a fluid is introduced into the dilation body 5 via the flow channel 51 so that the dilation body 5 is dilated in the radial direction.

Figure 5:
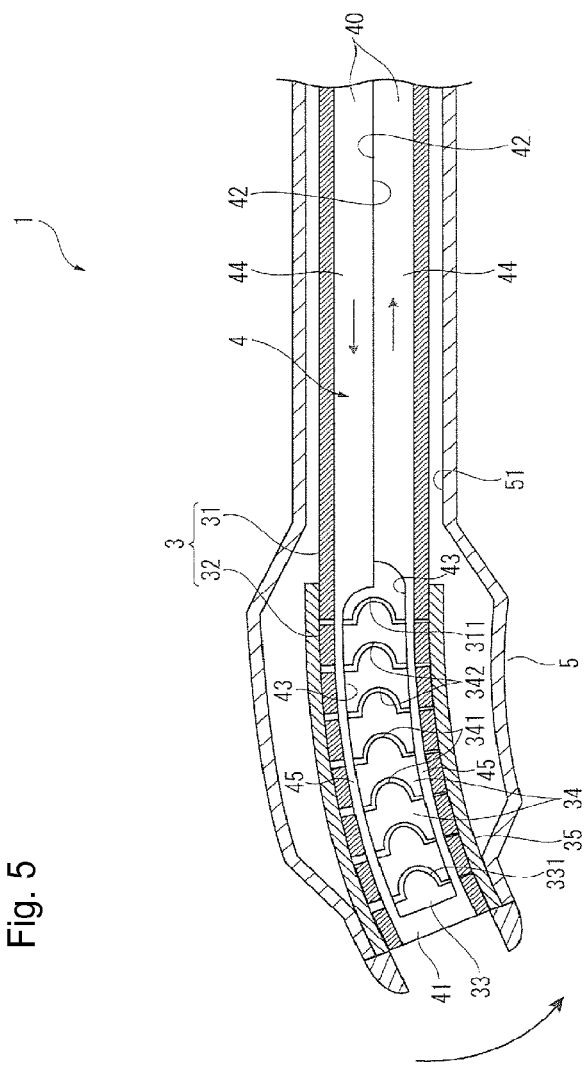
FIG. 5 is a side view showing a bent state of the insertion tube of the medical treatment tool of FIG. 1.

In the above medical treatment tool 1, the position fixture 23 is rotated with respect to the hub 2 when the flexible tube 32 of the insertion tube 3 is bent. If the position fixture 23 is rotated, as shown in FIG. 5, one divided member 40 of the operating body 4 is pushed to the distal side, and the other divided member 40 is pulled to the proximal side. For this reason, one divided member 40 and the other divided member 40 relatively move in the axial direction while the end edges 42 of the adjacent divided members 40 in the circumferential direction slide on each other in the axial direction. As a result, the flexible tube 32 can be bent as the narrow portions 45 of the operating body 4 are bent while the outer surface of the operating body 4 slides on the inner surface of the insertion tube 3. The bending position of the flexible tube 32 in this case can be fixed by the position fixture 23.

Next, the use procedure and operation of the medical treatment tool 1 when the medical treatment tool 1 is used as a treatment tool for rhinosinusitis treatment will be described as an example of use of the medical treatment tool 1.

First, an operator inserts the insertion tube 3 of the medical treatment tool 1 into a nostril. In this case, by inserting imaging means, such as an endoscope, into the insertion tube 3, the operator can insert the insertion tube 3 while confirming a state within an insertion path, on the basis of image information acquired by the imaging means.

If the dilation body 5 of the inserted insertion tube 3 is guided to a natural ostium of the paranasal sinus narrowed by rhinosinusitis, the operator introduces a fluid into the dilation body 5 via the flow channel 51, and dilates the dilation body 5, thereby dilating and treating a narrow segment of the natural ostium. In addition, if the insertion tube 3 is retreated a little after the dilation body 5 is contracted, whether the narrow segment was dilated can be confirmed from the image information acquired by the imaging means.

Also, if a fluid or sticky substance, such as mucous, remains in the paranasal sinus, the insertion tube 3 can be inserted into the paranasal sinus from the dilated natural ostium, and the fluid or sticky substance can be carried via the inner cavity of the insertion tube 3 and the fluid carrying path 22. Additionally, by introducing a washing fluid, such as a physiological salt solution, into the fluid carrying path 22, the fluid can also clean the inside of the paranasal sinus.

Advantages of the present embodiment may include the following.

That is, the operating body 4 forms the tubular structure by the plurality of divided members 40 that are divided in the circumferential direction, and each divided member 40 is provided with the cutout portions 43 formed such that the end edges 42 thereof in the circumferential direction are cut out. For this reason, the operating body 4 can be bent in low-rigidity portions where the cutout portions 43 are provided, and the tubular structure of the operating body 4 can be maintained in high-rigidity portions where the cutout portions 43 are not provided. Accordingly, since the operating body 4 can be prevented from obstructing the inner cavity while enabling the bending of the insertion tube 3 by the operating body 4, the inner cavity of the insertion tube 3 can be secured with simple structure.

Additionally, since the inner surface of the insertion tube 3 and the outer surface of the operating body 4 slide on each other at least partially in the axial direction, the tubular structure of the operating body 4 can be enlarged to the extent that the operating body 4 can come into contact with the inner surface of the insertion tube 3. Accordingly, since a large space can be secured inside the operating body 4, the inner cavity of the insertion tube 3 can be sufficiently secured.

Additionally, since the end edges 42 of the adjacent divided members 40 in the circumferential direction slide on each other, the tubular structure of the operating body 4 can be reliably maintained from the abutment between the end edges 42 of the divided members 40 in the circumferential direction, while the relative movement in the axial direction between the divided members 40 produced during the bending of the insertion tube 3 is allowed by the sliding. Accordingly, the operating body 4 can be prevented from blocking the inner cavity of the insertion tube 3 during the bending of the insertion tube 3.

Additionally, since the dilation body 5 can be dilated in the narrow segment in the body, the narrow segment can be dilated and treated.

Second Embodiment

Next, a second embodiment of the invention will be described with reference to FIG. 6.

Figure 6:
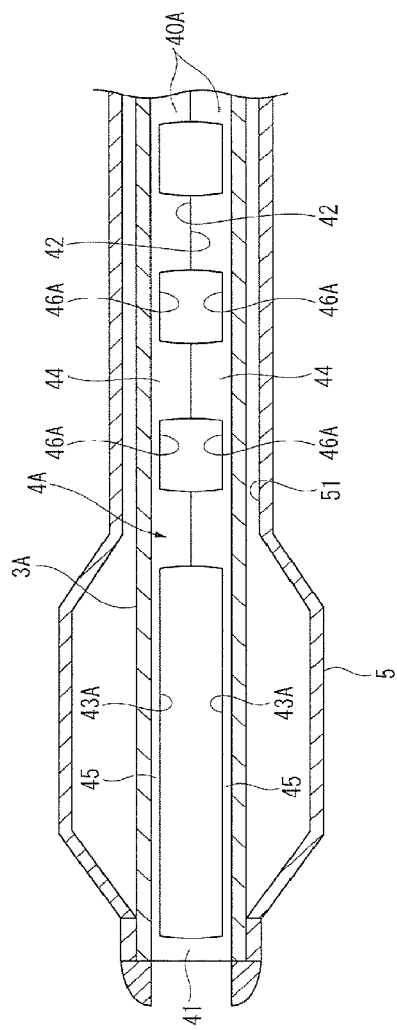
FIG. 6 is a side view of an insertion tube of a medical treatment tool related to a second embodiment of the invention.

A medical treatment tool 1A of the present embodiment, as shown in FIG. 6, is different from the tool in the first embodiment in terms of the structure of an insertion tube 3A and a plurality of cutout portions 43A and 46A provided in the axial direction of an operating body 4A.

The insertion tube 3A is made of a material having flexibility, such as resin or rubber, as a whole, and is configured so that an arbitrary portion is bendable.

On the other hand, in the operating body 4A, a plurality of cutout portions 43A and 46A are provided in the axial direction of each divided member 40A. In the present embodiment, the cutout portion 43A of each divided member 40A that is located furthest toward the distal end is formed to be long in the axial direction compared to the plurality of other cutout portions 46A according to the length of the dilation body 5 in the axial direction.

Additional advantages of the second embodiment may include the following.

That is, since the plurality of cutout portions 43A and 46A are provided in the axial direction of each divided member 40A, the operating body 4A can be intermittently bent at the positions of the respective cutout portions 43A and 46A. For this reason, since the bent shape of the insertion tube 3A can be changed by changing the arrangement of the cutout portions 43A and 46A in the axial direction, the bent shape of the insertion tube 3A can be set according to a path into which the insertion tube 3A is inserted.

Third Embodiment

Next, a third embodiment of the invention will be described with reference to FIG. 7.

Figure 7:
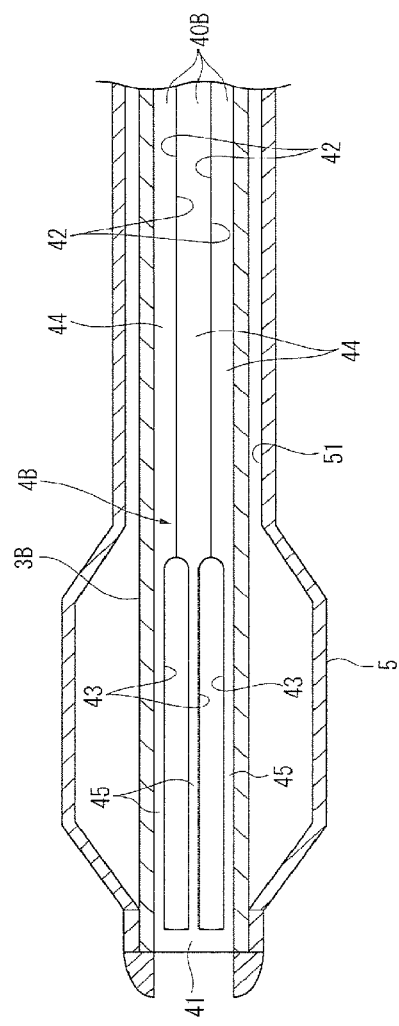
FIG. 7 is a side view of an insertion tube of a medical treatment tool related to a third embodiment of the invention.

A medical treatment tool 1B of the present embodiment, as shown in FIG. 7, is different from the first embodiment in terms of the structure of an insertion tube 3B and the number of divisions of divided members 40B of an operating body 4B.

The insertion tube 3B is configured similar to the second embodiment, and is made of a material having flexibility, such as resin or rubber, as a whole.

The operating body 4B is equally divided into four sections that form a tubular structure in the circumferential direction. That is, the operating body 4B includes four divided members 40B and a connecting portion 41 that connects distal portions of the divided members 40B. Since the other configuration of the operating body 4B is the same as that of the first embodiment, the additional description thereof will be omitted.

Additional advantages of the third embodiment may include the following.

That is, since the operating body 4B includes the divided members 40B that are divided into four sections in the circumferential direction, the operating body 4B can be bent in four directions. For this reason, since the insertion tube 3B can be more flexibly bent, the followability of the insertion tube 3B with respect to a path into which the insertion tube 3B is inserted can be improved.

Fourth Embodiment

Next, a fourth embodiment of the invention will be described with reference to FIG. 8.

Figure 8:
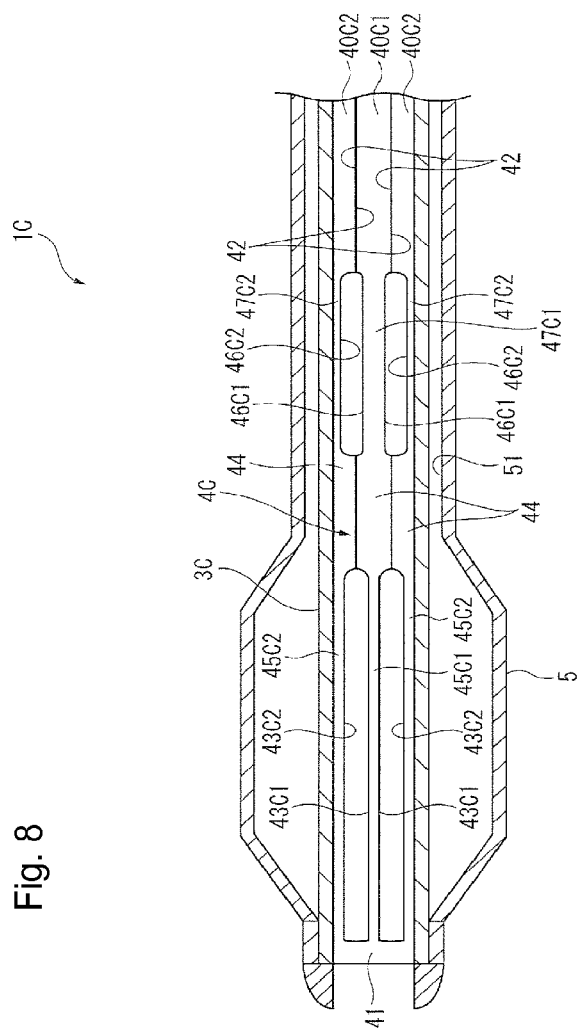
FIG. 8 is a side view of an insertion tube of a medical treatment tool related to a fourth embodiment of the invention.

A medical treatment tool 1C of the present embodiment, as shown in FIG. 8, is different from the first embodiment in terms of the structure of an insertion tube 3C and the number and shape of cutout portions 43C1, 43C2, 46C1, and 46C2 provided in the axial direction of an operating body 4C.

The insertion tube 3C is configured similar to the second embodiment, and is made of a material having flexibility, such as resin or rubber, as a whole.

The operating body 4C includes four divided members 40C1 and 40C2 in each of which two of the cutout portions 43C1, 43C2, 46C1, or 46C2 are provided in the axial direction, and the connecting portion 41 that connects distal portions of the divided members 40C1 and 40C2. Here, when two divided members 40C1 and 40C2 that face each other, are made into one set, the amounts of cutouts, in the circumferential direction, of the cutout portions 43C1 of the divided members 40C1 of one set are made larger than these of the cutout portions 43C2 of the divided members 40C2 of the other set, on the distal side of the operating body 4C. Additionally, on the proximal side of the operating body 4C, the amounts of cutouts, in the circumferential direction, of the cutout portions 46C2 of the divided members 40C2 of the other set are made larger than these of the cutout portions 46C1 of the divided members 40C1 of the other set.

By virtue of such a configuration, on the distal side of the operating body 4C, the circumferential dimensions of narrow portions 45C1 of the divided members 40C1 of the one set are made smaller than these of narrow portions 45C2 of the divided members 40C2 of the other set. Additionally, on the proximal side of the operating body 4C, the circumferential dimensions of narrow portions 47C2 of the divided members 40C2 of the other set are made smaller than these of narrow portions 47C1 of the divided members 40C1 of the one set. Also, in the respective divided members 40C1 and 40C2, the circumferential dimensions of the narrow portions 45C1 and 45C2 on the distal side are made different from the circumferential dimensions of the narrow portions 47C1 and 47C2 on the proximal side.

Additional advantages of the fourth embodiment may include the following.

That is, positions where the narrow portions 45C1 having smaller circumferential dimensions compared to the narrow portions 45C2 on the distal side of the operating body 4C are provided, and positions where the narrow portions 47C2 having smaller circumferential dimensions compared to these of the narrow portions 47C1 on the proximal side of the operating body 4C are provided are different from each other. For this reason, bending directions can be made different on the distal side and proximal side of the operating body 4C.

Fifth Embodiment

Next, a fifth embodiment of the invention will be described with reference to FIG. 9.

Figure 9:
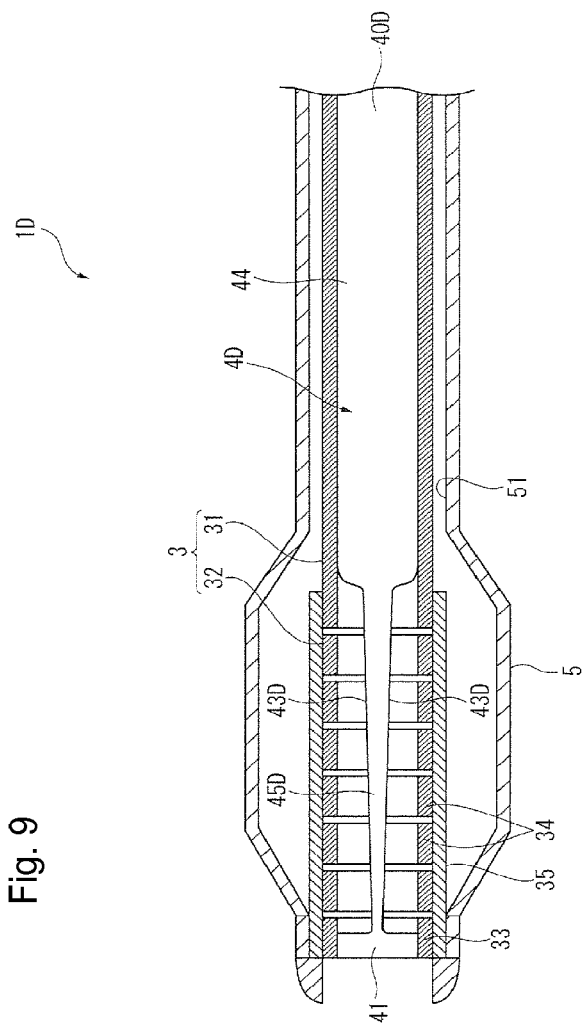
FIG. 9 is a side view of an insertion tube of a medical treatment tool related to a fifth embodiment of the invention.

A medical treatment tool 1D of the present embodiment, as shown in FIG. 9, is different from the first embodiment in terms of the shape of a narrow portion 45D of an operating body 4D, that is, the shape of cutout portions 43D of divided members 40D.

Specifically, the cutout portions 43D are formed so that the circumferential dimension of the narrow portion 45D becomes gradually smaller toward a distal portion in the axial direction. For this reason, the rigidity of the narrow portion 45 becomes gradually smaller toward the distal portion in the axial direction.

Additional advantages of the fifth embodiment may include the following.

That is, since the portion of each divided member 40D where the cutout portions 43D are provided, that is, the narrow portion 45D becomes gradually narrow toward the axial direction, the rigidity of the portion can be changed according to the degree of narrowness of the portion. For this reason, since the bent shape of the insertion tube 3 can be changed by changing the degree of narrowness of the portion, the bent shape of the insertion tube 3 can be set according to a path into which the insertion tube 3 is inserted.

Additionally, since the bending starting position of the operating body 4D during a bending operation can be changed by changes in the rigidity of the narrow portion 45D, the bending starting position of the insertion tube 3A can be set depending on the shape of the narrow portion 45D, that is, the shape of the cutout portions 43D. In addition, a portion that becomes gradually narrow may be provided not only at the distal portions of the cutout portions 43D but also at middle portions, proximal portions, or the like.

In the case of the present embodiment, since the rigidity of the narrow portion 45D becomes small toward a distal portion, the amount of bending becomes small at a proximal portion of the narrow portion 45D and becomes larger on the distal portion. For this reason, the bent state of the narrow portion 45D can be changed according to a position in the axial direction, and thereby, the bent shape of the insertion tube 3 can be changed.

Sixth Embodiment

Next, a sixth embodiment of the invention will be described with reference to FIG. 10.

Figure 10:
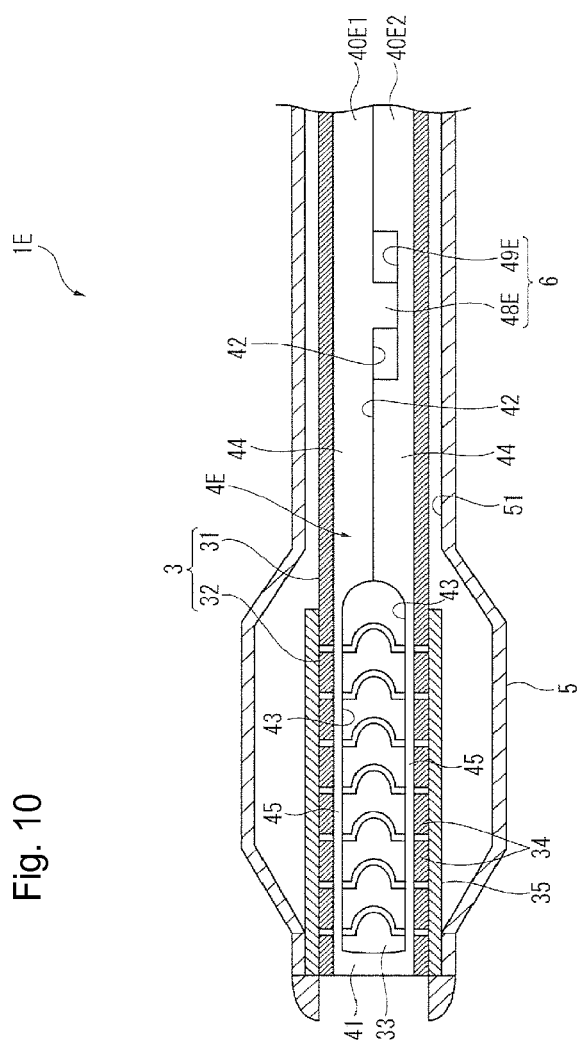
FIG. 10 is a side view of an insertion tube of a medical treatment tool related to a sixth embodiment of the invention.

A medical treatment tool 1E of the present embodiment, as shown in FIG. 10, is different from the first embodiment in that a movement regulating portion 6 is provided at end edges 42 of divided members 40E1 and 40E2 in an operating body 4E.

Specifically, the end edge 42 of the broad portion 44 of one divided member 40E1 is provided with a convex portion 48E protruding in the circumferential direction from the end edge 42. Additionally, the end edge 42 of the broad portion 44 of the other divided member 40E2 is provided with a concave portion 49E that is formed in a concave shape in the circumferential direction from the end edge 42 and has the convex portion 48E accommodated therein. Also, the movement regulating portion 6 is constituted by the convex portion 48E and the concave portion 49E.

Additional advantages of the sixth embodiment may include the following.

That is, since the movement regulating portion 6 that regulates the relative movement of the adjacent divided members 40E1 and 40E2 in the axial direction to a predetermined amount is provided, the bending amount of the insertion tube 3 can be regulated to the predetermined amount, and the bending limit of the insertion tube 3 can be defined.

Figure 11:
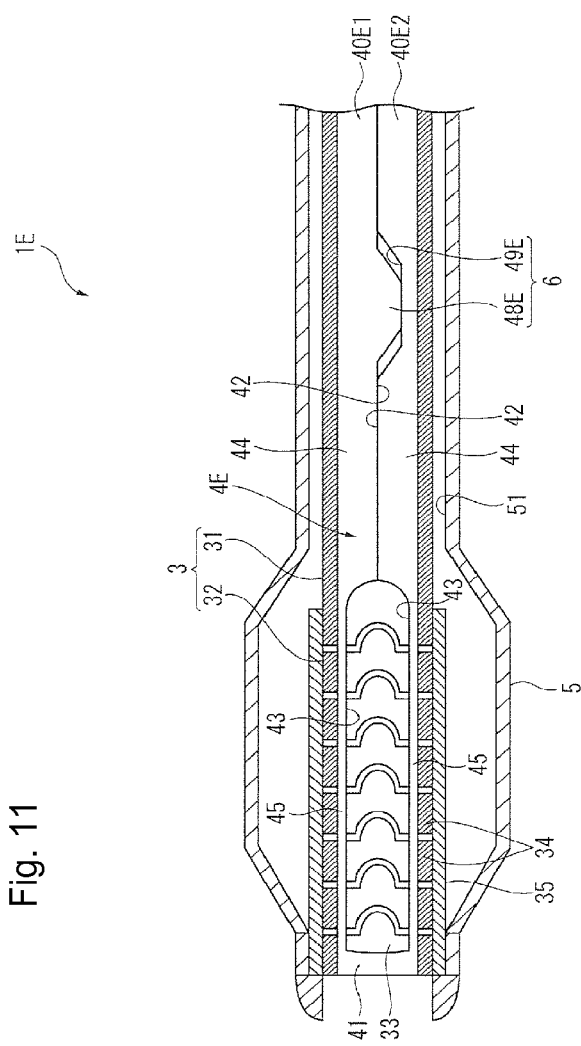
FIG. 11 is a side view of an insertion tube of a medical treatment tool related to a modification example of the sixth embodiment of the invention.

In addition, as shown in FIG. 11, as end edges of the convex portion 48E and the concave portion 49E in the axial direction are obliquely formed, the regulation of the relative movement of the divided members 40E1 and 40E2 can be performed not only by the abutment resistance of the convex portion 48E and the concave portion 49E but also by the diameter-enlargement resistance between the operating body 4E and the insertion tube 3 by the diameter enlargement of the operating body 4E. As a result, the bending limit of the insertion tube 3 can be more reliably defined, and the inner cavity of the insertion tube 3 can be sufficiently secured.

Seventh Embodiment

Next, a seventh embodiment of the invention will be described with reference to FIG. 12.

Figure 12:
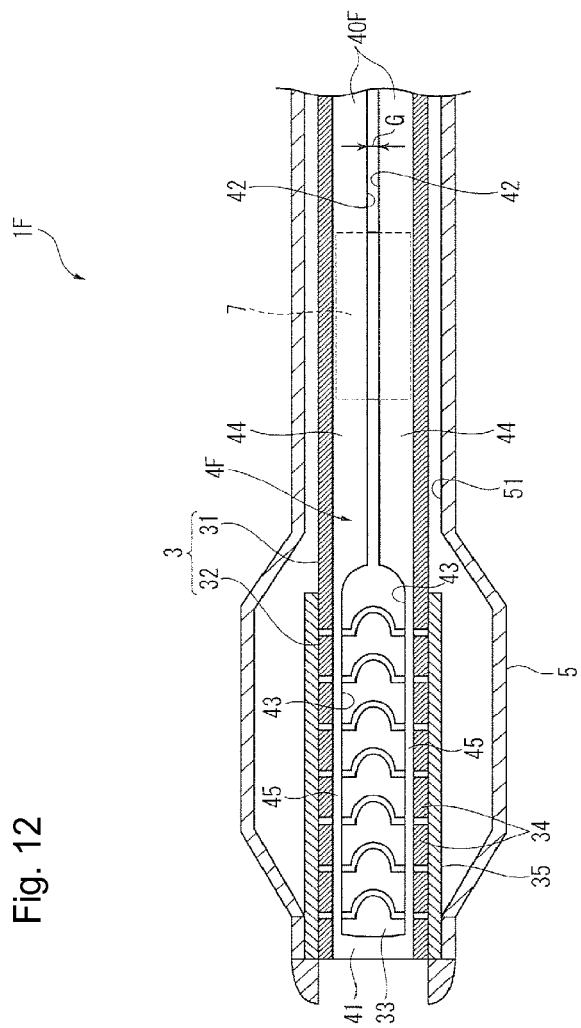
FIG. 12 is a side view of an insertion tube of a medical treatment tool related to a seventh embodiment of the invention.

A medical treatment tool 1F of the present embodiment, as shown in FIG. 12, is different from the first embodiment in that a cylindrical member 7 as an annular member is provided inside an operating body 4F and in that the end edges 42 of adjacent divided members 40F in the circumferential direction do not slide on each other.

The cylindrical member 7 has an external diameter that is large enough to have a gap G between the end edges 42 of the adjacent divided members 40F, and is provided inside the operating body 4F in the rigid tube 31. In addition, in the present embodiment, the cylindrical member 7 is attached to an inner surface of one divided member 40F. As a result, during the bending of the insertion tube 3, an inner surface of the other divided member 40F slides on an external surface of the cylindrical member 7, while the end edges 42 of the adjacent divided members 40F do not slide on each other.

Additional advantages of the seventh embodiment may include the following.

That is, since the cylindrical member 7 is provided inside the operating body 4F, the tubular structure of the operating body 4F can be maintained by the cylindrical member 7 even when there is the gap G between the end edges 42 of the adjacent divided members 40F in the circumferential direction. On the other hand, when there is no gap G between the end edges 42 of the adjacent divided members 40F in the circumferential direction, the tubular structure of the operating body 4F can be more reliably maintained by the cylindrical member 7. Accordingly, the inner cavity of the insertion tube 3 can be secured irrespective of the presence or absence of the gap G between the end edges 42 of the divided members 40F.

Eighth Embodiment

Next, an eighth embodiment of the invention will be described with reference to FIG. 13.

Figure 13:
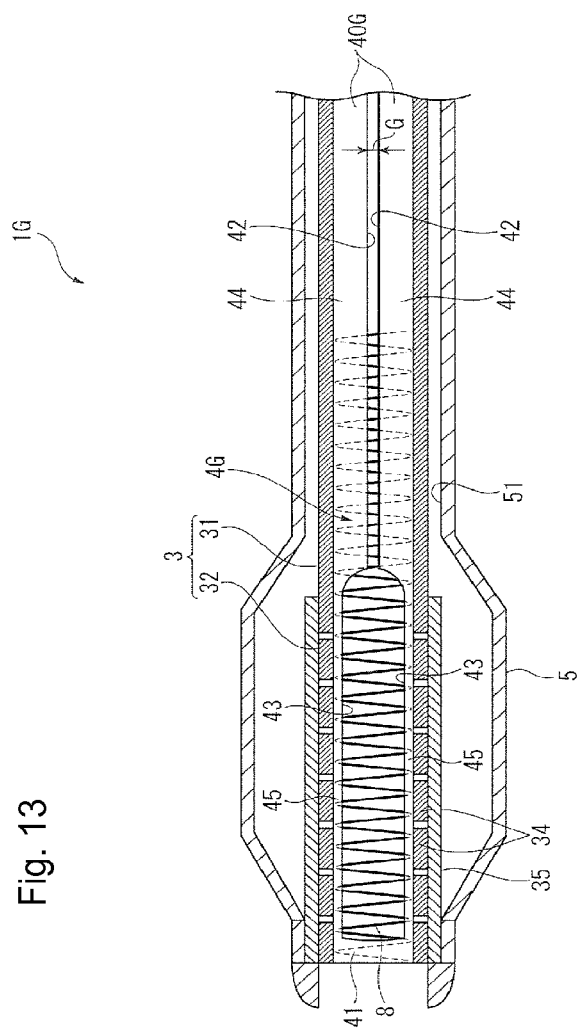
FIG. 13 is a side view of an insertion tube of a medical treatment tool related to an eighth embodiment of the invention.

A medical treatment tool 1G of the present embodiment, as shown in FIG. 13, is different from the seventh embodiment in that a coil spring 8 as an annular member is provided inside an operating body 4G.

The coil spring 8 has an external diameter that is large enough to have the gap G between the end edges 42 of adjacent divided members 40G and is provided from the connecting portion 41 of the operating body 4G to the broad portion 44 thereof.

Additional advantages of the eighth embodiment may include the following.

That is, since the coil spring 8 has flexibility, the spring can be arranged at any position of the rigid tube 31 and the flexible tube 32, and can be provided at arbitrary positions of the insertion tube 3.

Ninth Embodiment

Next, an eighth embodiment of the invention will be described with reference to FIG. 14.

A medical treatment tool 1H of the present embodiment, as shown in FIG. 14, is different from the first embodiment in that a balloon catheter 9 having a dilation body 91 is provided so as to be capable of being inserted into or pulled out of the tubular structure of the operating body in the insertion tube 3, and in that the dilation body 5 (FIG. 1) is not provided at an outer periphery of the insertion tube 3.

Additional advantages of the ninth embodiment may include the following.

That is, since the dilation body 91 is removably inserted into the tubular structure of the operating body 4, it is not necessary to provide the dilation body 5 (FIG. 1) at the outer periphery of the insertion tube 3. For this reason, the insertion tube 3 can be easily inserted inside the body in the dilation treatment of narrow segment.

In addition, the invention is not limited to the aforementioned embodiments, and alternations, improvements, or the like within the scope and the object of the invention will be included in the invention.

For example, although the insertion tube 3 and the operating body 4 are made of metal, such as stainless steel, the insertion tube and the operating body may be made of other members, such as resin and other metals as long as flexibility is provided.

Additionally, arbitrary insertion tubes can be used as the insertion tubes 3 and 3A to 3C as long as at least a portion is provided to be bendable. For example, in the aforementioned embodiments, the insertion tubes 3A to 3C that are bendably configured as a whole may be used instead of the insertion tube 3 including the flexible tube 32, or vice versa. Additionally, an insertion tube constituted by the flexible tube 32 as a whole may be used.

Moreover, the insertion tubes 3 and 3A to 3C do not need to be cylindrical, and may have a polygonal cross-section.

In the aforementioned embodiments, the operating bodies 4 and 4A to 4G include the divided members 40 and 40A to 40G that are divided into two or four. However, the number of divisions of the divided members is not limited to this if the number is equal to or more than two.

In the operating bodies 4 and 4A to 4G, the shape of the connecting portion 41 is not limited to those of the aforementioned embodiments. For example, the connecting portion may be formed in a tubular or linear fashion. Additionally, a plurality of linear members may be stretched between the respective divided members 40 and 40A to 40G so as to intersect the central axes of the tubular structures of the operating bodies 4 and 4A to 4G, and may constitute the connecting portion 41.

In the aforementioned embodiments, the dilation bodies 5 and 91 are provided. However, the dilation bodies 5 and 91 are not indispensable except for a case where dilation treatment of narrow segment is performed, and the medical treatment tools 1 and 1A to 1G may be configured without providing the dilation bodies 5 and 91.

In the aforementioned embodiments, when the cylindrical member 7 or the coil spring 8 as an annular member is provided inside the operating bodies 4F and 4G, the gap G is allowed between the end edges 42 of the adjacent divided members 40F and 40G. However, a configuration may be adopted in which the end edges 42 of the adjacent divided members 40 and 40A to 40G slide on each other after the annular members are provided inside the operating bodies 4 and 4A to 4G. As a result, the tubular structures of the operating bodies 4 and 4A to 4G can be more reliably maintained.

Additionally, the annular members are not limited to the cylindrical member 7 and the coil spring 8. For example, a plurality of fine linear annular members may be provided in the axial direction.

In the aforementioned embodiments, the medical treatment tools 1 and 1A to 1H are used for paranasal sinus observation, dilation of narrow segment produced in a natural ostium of the paranasal sinus, or treatment of the rhinosinusitis. However, the medical treatment tools may also be used for observation or treatment of other regions in the body.

Embodiment of the invention can be used in medical treatment tools, such as tools for treatment of a paranasal sinus. Embodiments of the invention can also be used for other medical examinations, or for treatments that do not accompany a surgical procedure.

What is claimed is:

1. A medical treatment tool comprising:
    a bendable tube configured to be inserted into a body of a patient;
    an operating body disposed in the bendable tube and configured to cause bending of the bendable tube, the operating body including:
        a plurality of divided members that are divided from each other along axially extending edges of adjacent divided members, portions of the divided members forming a tubular structure, and
        an annular connecting portion, an outer surface of the annular connecting portion being continuous with outer surfaces of the divided members; and
    a cylindrical member located inside the operating body,
    wherein each divided member comprises a cutout portion formed between the tubular structure and the annular connecting portion, and
    wherein the cylindrical member is in contact with inner surfaces of the divided members.

2. The medical treatment tool according to claim 1, wherein:
    the plurality of divided members comprises a first divided member and a second divided member; and
    an inner surface of the first divided member is attached to the cylindrical member, and an inner surface of the second divided member is configured to slide against the cylindrical member.

3. The medical treatment tool according to claim 1, wherein the cylindrical member has an external diameter such that a gap is located between the axially extending edges of the divided members.

4. The medical treatment tool according to claim 1, wherein an inner surface of the bendable tube and an outer surface of the operating body are configured to slide against each other in the axial direction.

5. The medical treatment tool according to claim 1, wherein the axially extending edges of the plurality of divided members are configured to slide against each other.

6. The medical treatment tool according to claim 1, wherein each divided member comprises a plurality of additional cutout portions.

7. The medical treatment tool according to claim 1, further comprising a dilation body that is located at an outer periphery of the bendable tube and is configured to dilate in a radial direction of the bendable tube.

8. The medical treatment tool according to claim 7, wherein the dilation body is a balloon extending around the cutout portion of each divided member.

9. The medical treatment tool according to claim 1, wherein the medical treatment tool is a treatment tool configured for rhinosinusitis treatment.

* * * * *